United States Patent [19]

Peck

[11] Patent Number: 4,821,733

[45] Date of Patent: Apr. 18, 1989

[54] TRANSDERMAL DETECTION SYSTEM

[75] Inventor: Carl C. Peck, Rockville, Md.

[73] Assignee: Dermal Systems International, Rockville, Md.

[21] Appl. No.: 87,699

[22] Filed: Aug. 18, 1987

[51] Int. Cl.$^4$ .............................................. A61B 5/00
[52] U.S. Cl. ..................................... 128/636; 128/760
[58] Field of Search ................ 128/632, 760, 636, 635

[56] References Cited

U.S. PATENT DOCUMENTS

| | | | |
|---|---|---|---|
| 3,993,049 | 11/1976 | Kater | 128/417 X |
| 4,036,227 | 7/1977 | Zaffaroni et al. | 424/21 X |
| 4,071,020 | 1/1978 | Pugliese | 424/9 X |
| 4,195,641 | 4/1980 | Joines et al. | 128/632 |
| 4,252,123 | 2/1981 | Kinnich | 128/635 |
| 4,273,134 | 6/1981 | Ricciardelli | 128/635 |
| 4,274,418 | 6/1981 | Vesterager et al. | 128/635 |
| 4,280,505 | 7/1981 | Pali et al. | 128/635 |
| 4,290,431 | 9/1981 | Herbert et al. | 128/635 |
| 4,329,999 | 5/1982 | Phillips | 128/760 |
| 4,396,017 | 8/1983 | Delpy et al. | 128/635 |
| 4,401,122 | 8/1983 | Clark, Jr. | 128/635 |
| 4,407,291 | 10/1983 | Hagihara et al. | 128/635 |
| 4,431,004 | 2/1984 | Bessman et al. | 128/635 |
| 4,444,193 | 4/1984 | Fogt et al. | 128/632 |
| 4,458,686 | 7/1984 | Clark, Jr. | 128/635 |
| 4,534,356 | 8/1985 | Papadakis | 128/635 |
| 4,539,994 | 9/1985 | Baumbach et al. | 128/635 |
| 4,556,056 | 12/1985 | Fischer et al. | 128/156 |
| 4,594,326 | 1/1986 | Wade | 128/632 X |
| 4,595,011 | 6/1986 | Phillips | 128/636 |

OTHER PUBLICATIONS

Abstract 3/9/82 Phillips et al.

Primary Examiner—William E. Wayner
Attorney, Agent, or Firm—Lowe, Price, LeBlanc, Becker & Shur

[57] ABSTRACT

A transdermal detection system for the detection of a target substance which migrates to the surface of the skin of a subject by diffusion comprises detector means and attachment means. The detector means includes at least one detector chemical contained in solution and capable of chemically reacting with the target substance as the target substance migrates to the skin surface of the subject to produce a detectable signal, and a barrier means for substantially preventing migration of the detector chemical into the skin surface of the subject. The attachment means maintains the detector means adjacent the surface of the skin of the subject.

26 Claims, 1 Drawing Sheet

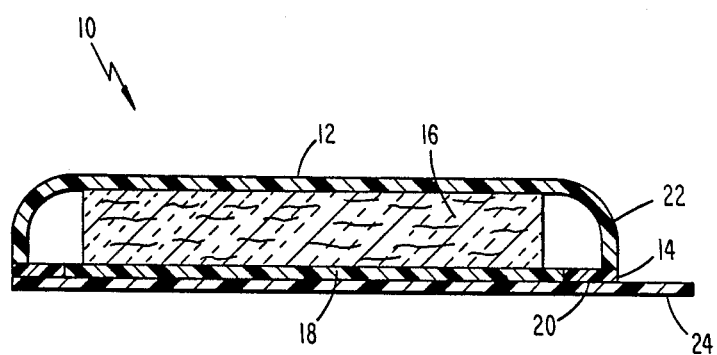

TRANSDERMAL DETECTION SYSTEM

FIELD OF THE INVENTION

The present invention relates to a transdermal detection system for the detection of a target substance which migrates to the surface of the skin of a subject by diffusion. More, particularly, the invention relates to a transdermal detection system which produces a detectable signal as the target substance migrates to the surface of the skin of the subject.

BACKGROUND OF THE INVENTION

Various transdermal devices and systems are known for collecting and monitoring body fluids. For example, in Peck et al, "A Non-Invasive Transepidermal Toxicological Monitoring Device", Pittsburgh Conference and Exposition on Analytical Chemistry and Applied Spectroscopy, Mar. 9, 1982, Meeting Abstracts Book, page 366, a transepidermal device is disclosed including an adhesive plastic chamber containing sodium chloride-impregnated absorbant pads and an activated charcoal impregnated disc for capturing a xenobiotic to prevent back transfer from the collection device into the body. The Peck copending application Ser. No. 660,778 filed Feb. 11, 1985 discloses a dermal substance collection device including a liquid bridge transfer medium for transferring a dermal substance to a binding reservoir material which binds the substance and prevents back transfer loss of the substance from the collection device.

The Phillips U.S. Pat. No. 4,329,999 discloses a dermal patch for collecting sweat from a patient which includes a collecting pad for absorbing sweat. Similarly, the Phillips U.S. Pat. No. 4,595,011 discloses a transdermal dosimeter device including a dermal contact bridge, a fluid collecting component for collecting and storing fluids collected from the skin and a process component for binding or chemically converting the stored substances. The latter Phillips patent suggests that chemical conversion of collected substances to produce an observable color change in the device may be effected.

The Fogt et. al. U.S. Pat. No. 4,444,193 discloses an absorbent patch device for absorbing sweat, which patch device includes a chemical composition capable of reacting with chloride contained in the sweat.

The Pugliese U.S. Pat. No. 4,071,020 discloses an apparatus and methods for performing in-vivo measurements of enzyme activity wherein one or more reactants are placed directly on a predetermined area of the skin surface and are free to migrate into the skin. While the apparatus and methods of Pugliese are not dependent on collection of a substance such as sweat or interstitial fluid, they may be dangerous to the subject if the reactants have toxic effects upon migration into the skin of the subject.

Other devices are also known for measuring substances, particularly gases, in or emanating from the skin. For example, the Clark, Jr. U.S. Pat. Nos. 4,401,122 and 4,458,686 disclose apparatus and methods for measuring substances, particularly gases, which diffuse through the skin or are present underneath the skin in the blood or tissue using polarographic electrodes or enzyme electrodes. The Vesterager et al U.S. Pat. No. 4,274,418 discloses an apparatus for measuring gases, for example oxygen and carbon dioxide, which diffuse from blood vessels and through skin tissue wherein the gas is directed to a measuring chamber in which the partial pressure is measured.

The present inventor has discovered that various substances migrate to the skin surface of a subject by diffusion in the absence of a liquid transport medium such as sweat and has discovered means for producing detectable signals in a transdermal detection system at the skin surface without direct placement of detector chemicals which are capable of migrating into the skin on the skin surface. Known transdermal devices rely on the collection of body fluids such as sweat or gaseous substances emanating from the skin or the binding of substances transferred through a liquid bridge transfer medium, without detection and signalling, or employ direct epidermal application of potentially toxic detector chemicals, and thus are disadvantageous for safely detecting and signaling substances which migrate to the skin surface of a subject by diffusion.

SUMMARY OF THE INVENTION

It is therefore an object of the present invention to provide a transdermal system for the detection of a substance which migrates to the skin surface of a subject by diffusion. It is a more specific object of the invention to provide a transdermal system for the detection of a substance which migrates to the skin surface of a subject by diffusion in the absence of a liquid medium such as sweat. It is a related object of the invention to provide a transdermal system for the detection of a substance which migrates to the surface of the skin of a subject by diffusion, which transdermal system does not rely on collecting a fluid from the skin surface and does not require direct placement of detector chemicals which can migrate into the skin on the skin surface in order to detect the target substance which has migrated to the skin surface of the subject.

These and additional objects are provided by the transdermal detection system according to the present invention which comprises an apparatus for detecting a target substance which has migrated to the surface of the skin of a subject by diffusion. The apparatus includes detector means and attachment means for maintaining the detector means adjacent to the surface of the skin of the subject. The detector means includes at least one detector chemical contained in solution and capable of chemically reacting with the target substance as the target substance migrates to the surface of the skin of the subject to produce a detectable signal, and barrier means for substantially preventing the detector chemical from migrating into the skin. The terminology "in solution" describes a uniformly dispersed mixture at the molecular or ionic level of one or more substances, the solute, in one or more other substances, the solvent, as is set forth in *The Condensed Chemical Dictionary*, 10th edition, G. G. Hawley, Van Nostrand Reinhold Co., 1981, pages 957-958. As is well-known in the art, common types of solutions include liquid/liquid, solid/liquid and solid/solid systems. In accordance with the apparatus of the present invention, the detector means is maintained adjacent to the skin surface of the subject by the attachment means, and the detector chemical contained in solution in the detector means is capable of chemically reacting with the target substance as the target substance migrates to the surface of the skin of the subject in order to produce a detectable signal. Thus, the apparatus of the invention is not dependent on the collection of sweat or other liquid transport medium in order to detect a target substance which migrates to the surface of the skin of a subject by diffusion. Additionally, the apparatus of the invention substantially prevents the detector chemical from migrating into the skin and avoids any toxic effects in the subject which would result from the detector chemical migrating the skin of the subject.

These and additional objects and advantages according to the present invention will become more apparent in view of the following detailed disclosure.

DESCRIPTION OF THE DRAWING

The following detailed description will be more fully understood in view of the Figure which sets forth one embodiment of the transdermal detection apparatus of the present invention. DETAILED DESCRIPTION As set forth above, the transdermal detection system of the present invention comprises an apparatus for the detection of a target substance which migrates to the surface of the skin of a subject by diffusion. The apparatus is particularly suitable for detecting a target substance which migrates to the surface of the skin of a subject by diffusion in the absence of a liquid transport medium such as sweat or interstitial fluid. The target substance may be any exogenous or endogenous chemical, or microbiological or biological material which has migrated to the surface of the skin by simple diffusion from within the body. The diffusion of the target substance need not be dependent on sweating or on collection of interstitial fluid.

The apparatus according to the invention comprises detector means including at least one detector chemical contained in solution and capable of chemically reacting with the target substance as the target substance migrates to the skin surface of the subject to produce a detectable signal. Depending on the target substance which is to be detected, the detector means may include a mixture of two or more detector chemicals contained in solution and capable of chemically reacting with the target substance as the target substance migrates to the surface of the skin of the subject to produce a detectable signal.

As set forth above, the term "in solution" refers to a uniformly dispersed mixture at the molecular or ionic level of one or more substances, the solute, in one or more other substances, the solvent. The detector chemical may comprise a chemical reagent such as an acid or a base, antibodies, enzymes, biological receptors, and/or mixtures thereof. The detector chemical may be in a liquid or solid state as long as it is contained in solution in a solvent as defined above. Preferred solvents comprise liquid aqueous solvents, for example, water or a saline solution, a gel or the like.

Suitable transdermal detection systems according to the present invention have been provided wherein the detector chemical provided in the detector means includes an oxidase enzyme contained in solution in an aqueous solvent. As is set forth in detail in the examples, a transdermal ethanol detection system may be provided wherein the detector chemical includes alcohol oxidase and a transdermal glucose detection system may be provided wherein the detector chemical includes glucose oxidase. Additionally, the detector chemical may suitably comprise a mixture of an oxidase and a peroxidase in solution in an aqueous solvent. Horseradish peroxidase, for example, may be used in combination with an alcohol or glucose oxidase in a specific embodiment of the detector means of the present invention.

The detector chemical contained in the detector means is capable of chemically reacting with the target substance as the target substance migrates to the surface of the skin of the subject to produce a detectable signal. The detectable signal which results may be, for example, an optically detectable signal such as a visible color change or an electrically detectable signal such as a pH change, i.e. a change in the hydrogen ion concentration, or other ion concentrations change. Other optically and electrically detectable signals which may result from the chemical reaction of the detector chemical with the target substance will be apparent to one skilled in the art and are included within the scope of the present invention.

The detector means of the present invention also includes a barrier means for substantially preventing the detector chemical from migrating into the skin of th subject. More particularly, the barrier means may comprise a microporous membrane containing covalent linking functional groups which covalently bind or link with the detector chemical to substantially prevent the detector chemical from migrating into the skin of the subject. Alternatively, the barrier means may comprise a permeable or semi-permeable membrane which allows passage of the target substance therethrough while substantially preventing passage of the detector chemical to the skin surface of the subject and therefore substantially prevents migration of the detector chemical into the skin. A suitable permeable membrane may be formed of a permeable material such as tissue paper while a suitable semipermeable membrane may comprise a semipermeable material such as a dialysis membrane. A semipermeable membrane such as a dialysis membrane provides a more complete prevention of migration of the detector chemical into the skin than the permeable tissue membrane. Alternatively, the barrier means may comprise a layer of gel, for example, a silicone gel or other suitable gel, for substantially preventing the detector chemical from migrating into the skin of the subject. The barrier means is a particularly important component of the apparatus of the invention since the migration of various detector chemicals into the skin of a subject may cause a toxic reaction in the subject.

The apparatus according to the present invention also includes attachment means for maintaining the detector means adjacent to the surface of the skin of the subject. Because the detector means is adjacent the surface of the skin of the subject, the detector chemical is available for chemically reacting with the target substance as the target substance migrates to the surface of the skin of the subject. The attachment means may comprise any components capable of maintaining the detector means adjacent the surface of the skin of the subject. In a preferred embodiment, the attachment means includes an adhesive area for adhesively maintaining the detector means adjacent to the surface of the skin of the subject. For example, one or more adhesive strips or an adhesive perimeter portion may be provided as the attachment means.

In one embodiment of the apparatus according to the present invention, the detector means further comprises a carrier which is saturated with the detector chemical contained in solution. Generally, the carrier acts as a physical support for the detector chemical contained in solution and is particularly suitable for use with solid/liquid solutions. The carrier may comprise a porous support member such as filter paper or the like or a microporous membrane similar to that described previously for use as the barrier means. For example, the carrier may comprise a microporous membrane containing covalent linking functional groups which covalently link or bind with the detector chemical to hold the detector chemical on the carrier. Thus, the carrier may also assist in preventing the detector chemical from migrating into the skin of the subject. The detector means comprising the carrier saturated with the detector chemical and the previously described barrier means, for example, a semipermeable or permeable membrane, are maintained adjacent the surface of the skin of the patient so that the detector chemical may chemically react with the target substance as the target substance migrates to the surface of the skin of the subject to produce a detectable signal. Collection of sweat or interstitial fluid containing the target substance is not necessary and, when a substantially saturated carrier is included in the detector means, sweat or interstitial fluid collection is not generally possible.

The apparatus according to the present invention may further include cover means for preventing loss of the detector chemicals from the apparatus and/or contamination of the apparatus from external environmental substances. For example, an impermeable cover means may be provided for covering the surfaces of the detector means which are not positionable adjacent the surface of the skin of the subject. Suitable impermeable cover means may comprise foil, an impermeable polymeric material or the like. Additionally, a removable impermeable cover means may be provided for covering the surface of the detector means which is positionable adjacent the surface of the skin of the subject. The removable cover serves to preserve the functionality of the detector chemicals and to prevent contamination of the apparatus during storage and prior to use. For example, a peelable foil or impermeable polymeric material may be provided on the surface of the detector means which is positionable adjacent the surface of the skin of the subject. The peelable material may then be removed from the apparatus prior to its use for the detection of a target substance migrating to the surface of the skin of the subject. In a preferred embodiment, removal of the removable impermeable cover exposes the detector means and the adhesive attachment means of the apparatus so that the adhesive means may then be applied to the skin surface for use of the apparatus in detecting a target substance.

The apparatus according to the invention may further include a signalling means which is capable of converting the detectable signal produced by the detector means into a form which is easily observable by the human eye. For example, a chemical compound may be included which is capable of reacting with the reaction product of the detector chemical and the target substance to produce a color change in a visible portion of the transdermal detection system. Furthermore, the signalling means may comprise a reflectance spectrometer for indicating a color change in the detector means or a pH or other electrode and meter for indicating a change in the hydrogen or other ion concentration in the detector means. Additionally, the signalling means may include a microprocessing unit for converting the detectable signal into a numerical measured value.

Attention is directed to the FIGURE which discloses one embodiment of the apparatus according to the present invention. The FIGURE discloses a transdermal detection apparatus 10 including detector means 12 and attachment means 14. The detector means 12 includes a porous carrier 16 formed of filter paper which is saturated with the detector chemical contained in solution and a barrier means 18 comprising a membrane material. The adhesive means 14 comprises an annular ring of a plastic polymeric material having an adhesive coating on its lower surface 20 which is adapted for positioning adjacent the surface of the skin of a subject. The apparatus further includes an impermeable cover 22 formed of an impermeable polymeric material which covers the surfaces of the detector means which are not positionable adjacent the surface of the skin of the subject. A removable impermeable cover 24 comprising a peelable material is also included in the apparatus and is adapted for removal from the apparatus prior to use for the detection of the target substance migrating to the surface of the skin of a subject. Once the cover 24 is removed from the apparatus, the adhesive surfaces 20 of the attachment means are positioned on the skin surface so that the detector means is maintained adjacent the surface of the skin of the subject, with barrier means 18 substantially preventing the detector chemical from migrating into the skin surface.

The present invention will be more fully understood in view of the following examples.

EXAMPLE 1

A transdermal ethanol detection system was prepared according to the present invention. The detector means comprised a carrier saturated with a mixture of detector chemicals contained in solution, and a barrier means for substantially preventing migration of the detector chemicals into the skin. Specifically, the carrier comprised a 5×7.5 mm. rectangular piece of filter paper (Whatman No. 40) saturated with a mixture of 1.1 units of an alcohol oxidase, 1 unit of horseradish peroxidase and 80 micrograms tetramethylbenzidine contained in solution in 30 ul of 0.04 Molar potassium phosphate monobasicsodium phosphate dibasic buffer (pH 7.41) in 3% saline solution. The barrier means comprised a 1.1 cm. circular permeable membrane of Kimwipe material (supplied by Kimberly-Clark Corporation). An impermeable cover comprising Saran Wrap (supplied by Dow Chemical Co.) was also included. The attachment means comprised an annular disc member having adhesive on both sides (Double-Stick Disc supplied by 3M Corporation), a 1.25 inch outer diameter and an 11/32 inch inner aperture in which the detector means was positioned.

The transdermal ethanol detection system as described above may be attached to the skin surface of a subject in order to detect ethanol which migrates to the surface of the skin of a subject by diffusion. When the apparatus is placed on the skin surface, the detector means often turns from a light bluish-green color to a pale cream color. It is believed that this color change is caused by a change in the apparatus temperature from room temperature (23°-25° C.) to the skin surface temperature (30°-32° C.). The color will generally remain unchanged if no ethanol migrates to the skin surface of the subject. However, as ethanol migrates to the skin surface by diffusion, the detector means changes to an increasingly dark green to purple-blue color. For example, when attached to the skin of a person drinking alcohol at the rate of one and a half beers per hour, the detector means changed to a dark green-blue color within two to three hours after intake commencement. Additionally, the detector means has turned a green-blue color within 30 minutes of attaching the apparatus to the skin of a subject who has already consumed three or more beers at a rate of one and a half beers per hour. The color change was clearly visible to the naked eye while the apparatus was still attached to the subject. The color change was also measured by removing the detector means from the apparatus and measuring the decrease in reflectance of an infrared beam emitted at 940 NM in a reflectance spectrometer (Diascan Blood Glucose Self-Monitoring Meter supplied by Home Diagnostics Inc., Eatontown, N.J.). Relative to a control specimen having no contact with ethanol, the apparatus registered a 5 to 30% unit decrease in percent transmittance of the infrared beam, the magnitude of the decrease depending upon the amount of ethanol which had been consumed by the subject. In this example, the target substance migrated to the skin surface by diffusion in the absence of sweat.

In the transdermal ethanol detection system of this example, the disclosed barrier means or the carrier may be replaced with a microporous membrane containing covalent linking functional groups. An example of such a membrane is the Pall Immunodyne Affinity Membrane supplied by Pall Biosupport Division, East Hills, N.J. The binding of the alcohol oxidase, horseradish peroxidase and tetramethylbenzidine to the microporous membrane assists in preventing migration of these components into the skin. Thus, the microporous membrane is a particularly suitable carrier or barrier means when a detector chemical is highly toxic to the subject on migration into the skin. The barrier means used above may also be replaced with a dialysis membrane such as the Spectra/Por 6 membranes supplied by Fischer Scientific, Silver Spring, Md. (exhibiting a molecular weight cut off of 1000) which substantially prevents the detector chemicals which are unable to pass through the membrane from migrating into the skin.

EXAMPLE 2

A transdermal glucose detection system according to the present invention is prepared wherein the detector means includes a porous carrier saturated with a mixture of glucose oxidase, horseradish peroxidase and tetramethylbenzidine contained in solution in a buffered saline solvent, and a barrier means. Specifically, the carrier comprises a 5×7.5 mm rectangular piece of filter paper (Whatman No. 40) impregnated with one unit of glucose oxidase, 1.5 units of horseradish peroxidase and 80 ug of tetramethylbenzidine contained in solution in 30 ul of 0.03 Molar sodium acetate buffer (pH of 5.2) in 3% saline. A barrier means comprising a membrane as set forth in Example 1 is included in the detector means, and the attachment means comprises an annular adhesive tape as described in Example 1. An impermeable plastic cover is also provided.

The transdermal glucose detection system may be attached to the skin surface of a subject for a predetermined time period, for example, six to twelve hours. Initially, the detector means will often turn from a light bluish-green color to a pale cream color. It is believed that this slight color change occurs as a result of the change in temperature of the apparatus from room temperature (23°-25° C.) to the temperature of the skin surface (30°-32° C.). When attached to the skin of a nondiabetic subject, the color of the detector means will remain a pale cream color or exhibit only a slight color change to a very pale green. However, when attached to the skin surface of a diabetic subject, the color of the detector means will change to an increasingly dark green-blue color as glucose migrates to the skin surface. The color change could also be measured as set forth in Example 1 by measuring the decrease in reflectance of an infrared beam. The target substance will migrate to the skin surface by diffusion in the absence of sweat. As set forth in Example 1, the disclosed barrier means or carrier used in the present example may be replaced with a microporous membrane. The permeable membrane barrier means may also be replaced with a semipermeable membrane barrier layer.

The preceding examples are set forth to illustrate specific embodiments of the invention and are not intended to limit the scope of the apparatus and method of the present invention. Additional embodiments and advantages within the scope of the claimed invention will be apparent to one of ordinary skill in the art.

What is claimed is:

1. An apparatus for the detection of a target substance which migrates to the surface of the skin of a subject by diffusion, comprising detector means including (a) at least one detector chemical contained in solution and capable of chemically reacting with the target substance as the target substance migrates to the surface of the skin of the subject to produce a detectable signal and (b) a barrier means for substantially preventing said detector chemical from migrating into the skin of the subject; and attachment means for maintaining the detector means adjacent the surface of the skin of the subject.

2. An apparatus as defined by claim 1, wherein the detector means is capable of chemically reacting with the target substance as the target substance migrates to the surface of the skin of the subject to produce an electrically detectable signal.

3. An apparatus as defined by claim 2, wherein the detector means is capable of chemically reacting with the target substance as the target substance migrates to the surface of the skin of the subject to produce an electrically detectable change in an ion concentration in the detector means.

4. An apparatus as defined by claim 1, wherein the detector means further comprises a carrier substantially saturated with the detector chemical contained in solution and capable of chemically reacting with the target substance as the target substance migrates to the surface of the skin of the subject.

5. An apparatus as defined by claim 4, wherein the carrier comprises a porous support member.

6. An apparatus as defined by claim 5, wherein the carrier comprises a microporous membrane containing covalent functional groups capable of covalently binding with the detector chemical contained in solution.

7. An apparatus as defined by claim 1, wherein the barrier means comprises a permeable or a semipermeable membrane.

8. An apparatus as defined by claim 1, wherein the barrier means comprises a layer of gel.

9. An apparatus as defined by claim 1, wherein the barrier means comprises a microporous membrane containing covalent functional groups capable of covalently binding with the detector chemical contained in solution.

10. An apparatus as defined by claim 1, wherein the detector chemical is selected from chemical reagents, antibodies, enzymes and biological receptors and is contained in solution in a solvent.

11. An apparatus as defined by claim 1, wherein the detector means includes a mixture of detector chemicals contained in solution and capable of chemically reacting with the target substance as the target substance migrates to the surface of the skin of the subject to produce a detectable signal.

12. An apparatus as defined by claim 1, wherein the attachment means includes an adhesive area for adhesively maintaining the detector means adjacent the surface of the skin of the subject.

13. An apparatus as defined by claim 1, further comprising an impermeable cover means covering the surfaces of the detector means which are not positionable adjacent the surface of the skin of the subject.

14. An apparatus as defined by claim 1, further including a removable impermeable cover means covering the surface of the detector means which is positionable adjacent the surface of the skin of the subject, which removable cover means is adapted to be removed from the apparatus prior to use for the detection of a target substance migrating to the surface of the skin of the subject.

15. An apparatus as defined by claim 1, further including a signalling means capable of converting the detectable signal produced by the detector means into a form which is observable by the human eye.

16. An apparatus as defined by claim 15, wherein the signalling means includes microprocessing means.

17. An apparatus for the detection of a target substance which migrates to the surface of the skin of a subject by diffusion, comprising
   detector means including (a) at least one detector chemical contained in solution and capable of chemically reacting with the target substance as the target substance migrates to the surface of the skin of the subject to produce an optically detectable signal and (b) a barrier means for substantially preventing said detector chemical from migrating into the skin of the subject; and
   attachment means for maintaining the detector means adjacent the surface of the skin of the subject.

18. An apparatus as defined by claim 17, wherein the detector means is capable of chemically reacting with the target substance as the target substance migrates to the surface of the skin of the subject to produce a visually detectable color change in the detector means.

19. An apparatus for the detection of a target substance which migrates to the surface of the skin of a subject by diffusion, comprising
   detector means including (a) at least one detector chemical contained in solution and capable of chemically reacting with the target substance as the target substance migrates to the surface of the skin of the subject to produce a detectable signal, said detector chemical being selected from chemical reagents, antibodies, enzymes and biological receptors contained in solution in a solvent and including an oxidase in solution in a solvent, and (b) a barrier means for substantially preventing said detector chemical from migrating into the skin of the subject; and
   attachment means for maintaining the detector means adjacent the surface of the skin of the subject.

20. An apparatus as defined by claim 19, wherein the oxidase is selected from alcohol oxidases and glucose oxidases.

21. An apparatus for the detection of a target substance which migrates to the surface of the skin of a subject by diffusion, comprising
   detector means including (a) at least one detector chemical including a mixture of an oxidase and a peroxidase contained in solution in an aqueous solvent and capable of chemically reacting with the target substance as the target substance migrates to the surface of the skin of the subject to produce a detectable signal and (b) a barrier means for substantially preventing said detector chemical from migrating into the skin of the subject; and
   attachment means for maintaining the detector means adjacent the surface of the skin of the subject.

22. An apparatus as defined by claim 21, wherein the oxidase is selected from alcohol oxidases and glucose oxidases.

23. An apparatus as defined by claim 21, wherein the peroxidase comprises horseradish peroxidase.

24. An apparatus for the detection of ethanol which migrates to the surface of the skin of a subject by diffusion, comprising
   detector means including (a) detector chemicals comprising an alcohol oxidase, horseradish peroxidase and tetramethylbenzidine contained in solution and capable of chemically reacting with the ethanol as the ethanol migrates to the surface of the skin of the subject to produce a detectable color change and (b) a barrier means for substantially preventing migration of said detector chemicals into the skin of the subject; and
   attachment means for maintaining the detector means adjacent the surface of the skin of the subject.

25. An apparatus for the detection of glucose which migrates to the surface of the skin of a subject by diffusion, comprising
   detector means including (a) detector chemicals comprising glucose oxidase, horseradish peroxidase and tetramethylbenzidine contained in solution and capable of chemically reacting with the glucose as the glucose migrates to the surface of the skin of the subject to produce a detectable color change and (b) a barrier means for substantially preventing migration of said detector chemicals into the skin of the subject; and
   attachment means for maintaining the detector means adjacent the surface of the skin of the subject.

26. A method for the detection of a target substance which migrates to the surface of the skin of a subject by diffusion, comprising maintaining a detector means adjacent the surface of the skin of the subject, the detector means including (a) at least one detector chemical contained in solution and capable of chemically reacting with the target substance as the target substance migrates to the surface of the skin of the subject to produce a detectable signal, and (b) a barrier means for substantially preventing migration of said detector chemical into the skin of the subject.

* * * * *